Figures 3F, 3G, 3H:
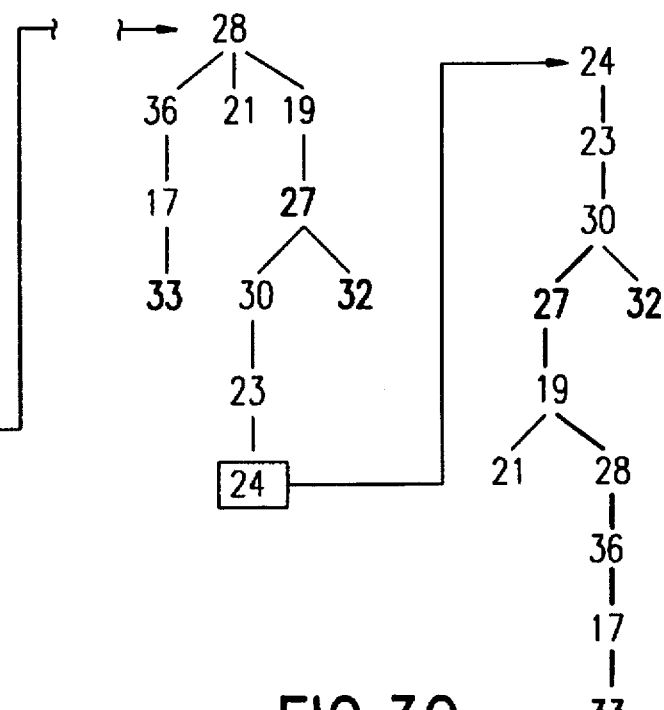

US005667970A

United States Patent [19]

Zhang

[11] Patent Number: 5,667,970
[45] Date of Patent: Sep. 16, 1997

[54] METHOD OF MAPPING DNA FRAGMENTS

[75] Inventor: Peisen Zhang, New York, N.Y.

[73] Assignee: The Trustees of Columbia University in the City of New York, New York, N.Y.

[21] Appl. No.: 240,864

[22] Filed: May 10, 1994

[51] Int. Cl.$^6$ ................................................. C12Q 1/68
[52] U.S. Cl. ......................................................... 435/6
[58] Field of Search .................................. 435/6, 501

[56] References Cited

U.S. PATENT DOCUMENTS 5,219,726  6/1993  Evans ............................. 435/6

OTHER PUBLICATIONS

Zhang et al., 1993, "An Alogorithm Based On Graph Theory For The Assembly of Contigs In Physical Mapping of DNA", in *Abstracts of Papers Presented At The 1993 Meeing on Genome Mapping and Sequencing*, Cold Spring Harbor Laboratory, Cold Spring Harbor, NY, p. 280.
Korte et al., SIAM J. Comput. (1989), vol. 18 (1): pp. 68–81.
Olson et al., 1986, Proc. Natl. Acad. Sci. 83: 7826–7830, "Random–clone Strategy for Genomic Restriction Mapping in Yeast ".
Cuticchia et al., 1992, Genetics, 132:591–601, "The Use of Simulated Annealing in Chromosome Reconstruction Experiments Based on Binary Scoring".
Mott et al., 1993, Nucleic Acids Research, 21:1965–1974, "Alogorithms and Software Tools for Ordering Clone Libraries: Application to the Mapping of the Genome of Schizosaccharomyces Pompe".

*Primary Examiner*—Mindy Fleisher
*Assistant Examiner*—Terry A. McKelvey
*Attorney, Agent, or Firm*—Brumbaugh, Graves, Donohue & Raymond

[57] ABSTRACT

The present invention relates to a method of ordering DNA fragments in which binary overlap information, obtained by determining whether pairs of fragments hybridize to each other, is used to build a "spanning path" across a parent DNA molecule by successively attaching cloned fragments which overlap. The relative position of the many other, non-path fragments is not essential information, but can be determined. Means for eliminating false positives and false negatives is provided. The overlap relationships between fragments may be depicted as an interval graph.

12 Claims, 9 Drawing Sheets

Microfiche Appendix Included
(1 Microfiche, 35 Pages)

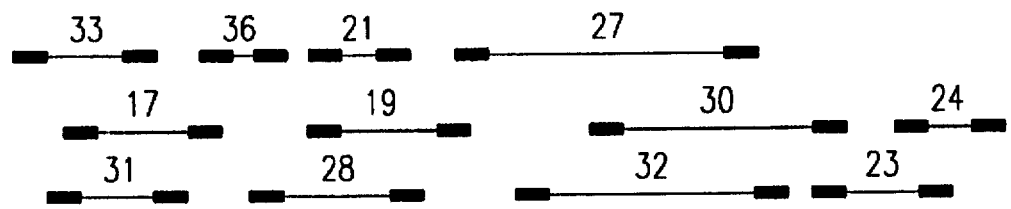
FIG.1A
| COSMID | COSMID OVERLAPS |
|---|---|
| 17 | 31,33,36 |
| 19 | 21,27,28 |
| 21 | 19,28 |
| 23 | 24,30 |
| 24 | 23 |
| 27 | 19,30,32 |
| 28 | 19,21,36 |
| 30 | 23,27,32 |
| 31 | 17,33 |
| 32 | 27,30 |
| 33 | 17,31 |
| 36 | 17,28 |
FIG.1B
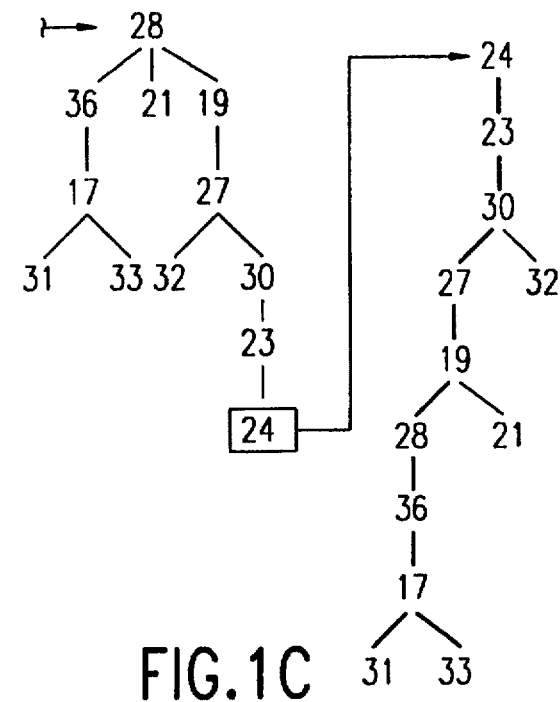
FIG.1C
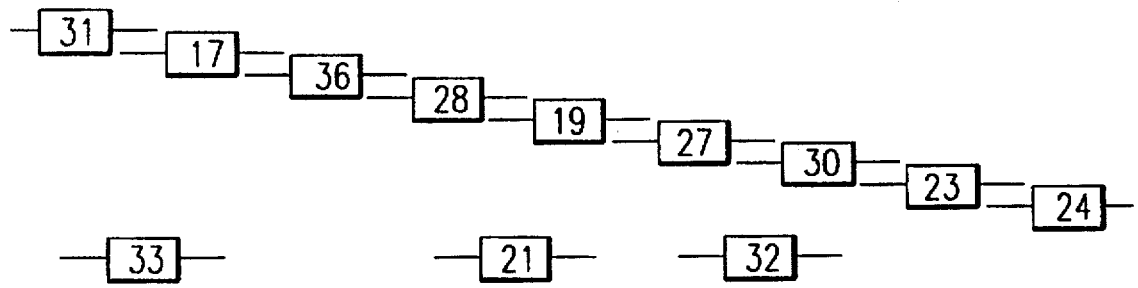
FIG.1D

FIG.1E

FIG.1F

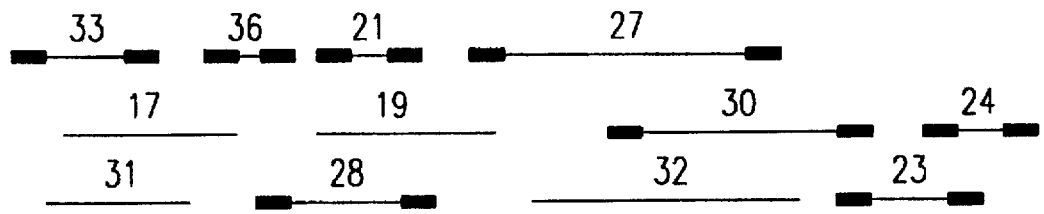
FIG.2A
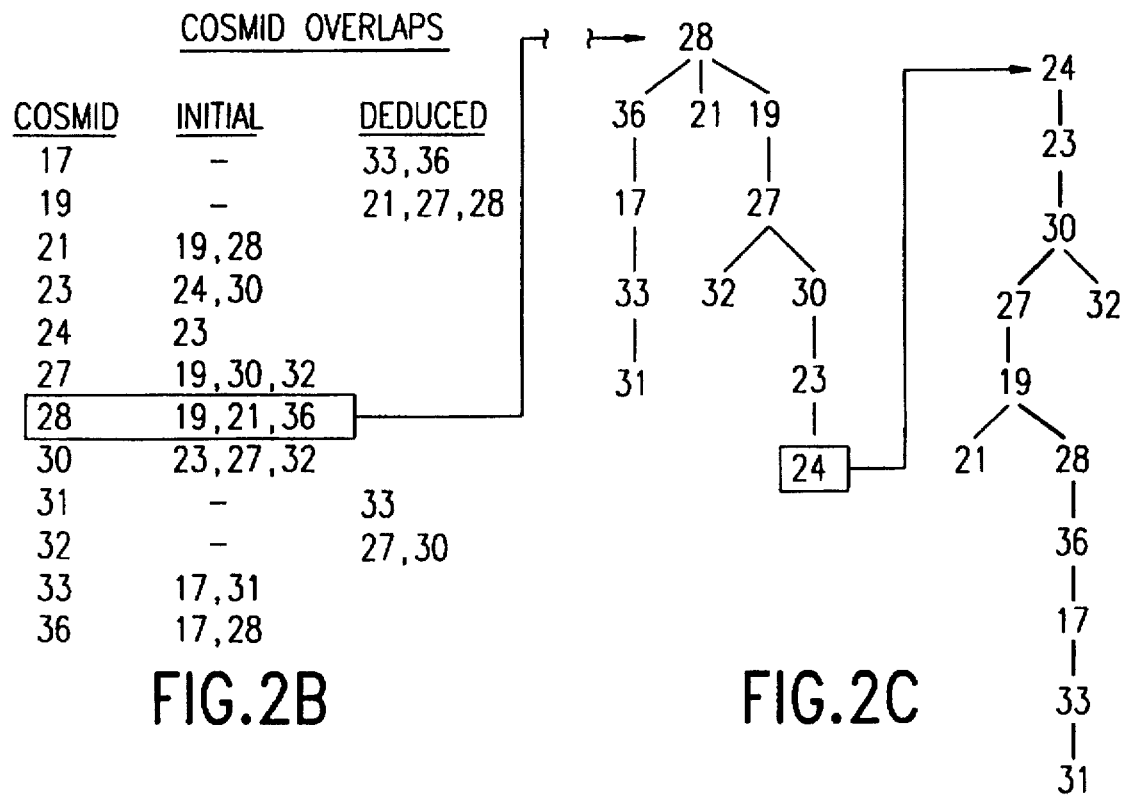
FIG.2B
FIG.2C
FIG.2D

FIG.2E

FIG.2F

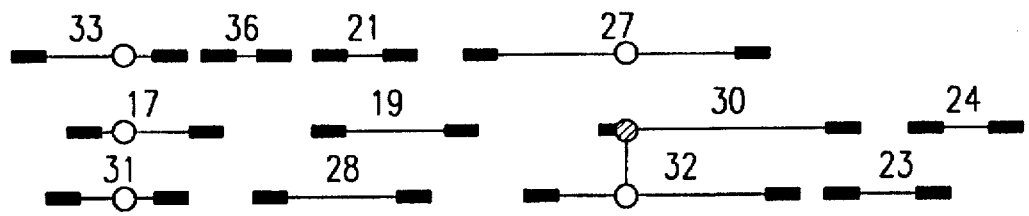
FIG.3A
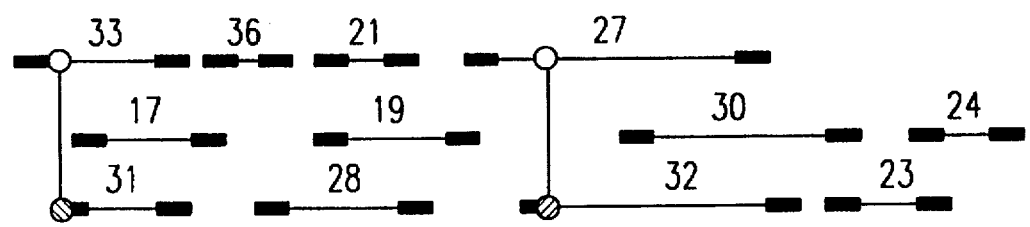
FIG.3B
| COSMID | COSMID OVERLAPS |
|---|---|
| 17 | 31,33,36 |
| 19 | 21,27,28 |
| 21 | 19,28 |
| 23 | 24,30 |
| 24 | 23 |
| 27 | 19,30,32 |
| 28 | 19,21,36 |
| 30 | 23,27,32 |
| 31 | 17,~~27~~,32,33 |
| 32 | 27,30,31,~~33~~ |
| 33 | 17,31 |
| 36 | 17,28 |
FIG.3C
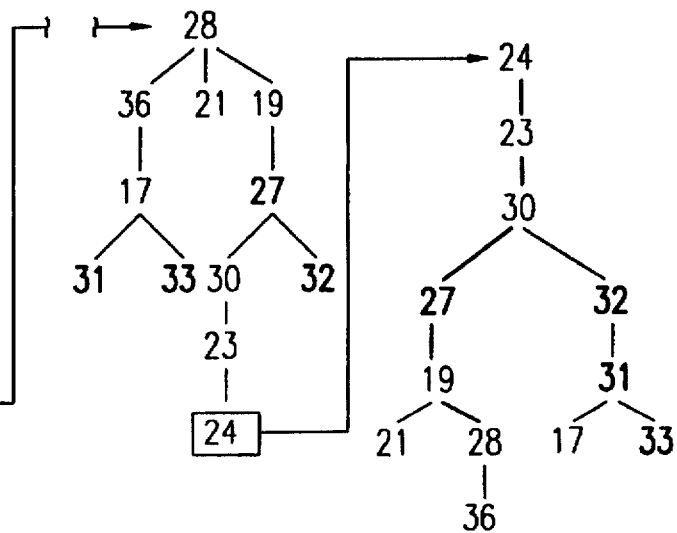
FIG.3D
( 36-28-19-27-30-23-24 )
FIG.3E

| COSMID | COSMID OVERLAPS |
|---|---|
| 17 | ~~31~~,33,36 |
| 19 | 21,27,28 |
| 21 | 19,28 |
| 23 | 24,30 |
| 24 | 23 |
| 27 | 19,30,32 |
| 28 | 19,21,36 |
| 30 | 23,27,32 |
| ~~31~~ | ~~17,27,32,33~~ |
| 32 | 27,30,~~31,33~~ |
| 33 | 17,~~31~~ |
| 36 | 17,28 |

33-17-36-28-19-27-30-23-24

FIG.4A

|-2f2-|
　　|-2b3-|
　　　　|-2a9-|
　　　　　|-2b8-|
　　　　　　|-2e4-|
　　　　　　　|-2c4-|
　　　　　　　　|-2f9-|
　　　　　　　　　|-2e8-|
　　　　　　　　　　|-2f4-|
　　　　　　　　　　　|-2a8-|
　　　　　　　　　　　　|-2a4-|
　　　　　　　　　　　　　|-2b7-|
　　　　　　　　　　　　　　|-2d7-|
　　　　　　　　　　　　　　　|-2f7-|
　　　　　　　　　　　　　　　　|-2c10-|
　　　　　　　　　　　　　　　　　|-2b10-|
　　　　　　　　　　　　　　　　　　|-2d4-|

FIG.4B

FIG.4C

METHOD OF MAPPING DNA FRAGMENTS

This application contains a Microfiche Appendix having 1 microfiche and 35 frames.

1. INTRODUCTION

The present invention relates to a method of ordering DNA fragments in which binary overlap information, obtained by determining whether pairs of fragments hybridize to each other, is used to build a "spanning path" across a parent DNA molecule.

2. BACKGROUND OF THE INVENTION

Nucleic acid sequencing technology has evolved to the point where sequencing large blocks of DNA, whole chromosomes, and even entire complex genomes have become reasonable objectives. Such ambitious sequencing projects involve strategies which require, first, that the subject DNA be cleaved into smaller, more manageable fragments and, second, that these fragments be used to construct a map in which the positions of fragments in the parent molecule are identified.

The map of ordered fragments provides useful information even before any nucleotide sequence is obtained, because the position of genes along the map can be determined. In addition, areas of particular interest in the map can be identified and given priority for sequencing.

The mapping process begins by cutting the parent DNA into fragments and then creating "libraries" of cloned DNA fragments contained in replicable vector molecules. Suitable vectors include yeast artificial chromosomes ("YACs"), cosmids, bacteriophage, and plasmids.

Next, to obtain a map of the location of fragments in the parent DNA molecule, the fragments must be assembled in their proper order, a task which increases in complexity as the size of the parent DNA molecule grows larger.

The ordering of cloned fragments is rendered feasible by the fact that most libraries are "redundant", in that instead of only one parent DNA molecule being cut into pieces, several parent molecules are each cut into fragments at different points. As a result, a library contains overlapping fragments. By identifying fragments that overlap, the parent molecule can be pieced together.

Although reconstruction of the parent molecule by joining consecutive fragments may seem conceptually simple, in practice, particularly for large parent DNA molecules, it is a formidable process. There frequently are hundreds or thousands of cloned fragments which must be placed in order, and, for a number of reasons, false overlaps may be detected and true overlaps may be missed. A number of ordering methods have been designed, each bearing their own particular advantages and disadvantages.

One approach (Olson et al., 1986, Proc. Natl. Acad. Sci. U.S.A. 83:7826-7830) involves cutting the DNA of a cloned fragment with one or more enzymes, termed "restriction endonucleases", which cleave DNA at specific short subsequences. Each cloned fragment will give rise to a characteristic set of so-called "restriction fragments" of particular sizes; this set of restriction fragments is sometimes referred to as a "DNA fingerprint". The cloned fragments are ordered by comparing DNA fingerprints. If certain sizes of restriction fragments are shared among two or more clones, those clones are deemed likely to contain overlapping DNA sequence. Important shortcomings of this method lie, first, in the potential for error associated with determining the sizes of restriction fragments and, second, in the fact that identically sized fragments need not contain the same nucleotide sequence.

Another ordering strategy (Cuticchia et al., 1992, Genetics 132:591-601) orders cloned DNA fragments not by comparing restriction fragment sizes, but by comparing the ability of cloned DNA fragments to hybridize to a series of detectably labelled nucleic acid probes consisting of short pieces of DNA sequence. The ability or inability of a particular clone to hybridize to each member of a panel of different oligonucleotide probes is determined and digitally recorded. The results of hybridization between a single cloned fragment and a multitude of oligonucleotide probes gives rise to a digital signature. Because the degree of overlap between two clones should be reflected by a similarity in their signatures, a number of clones may be ordered by quantitating, by statistical mechanics, and then minimizing the calculated differences in signatures across a reconstructed chromosome. This method, which requires an abundance of data and complicated calculations, is referred to as "simulated annealing".

Mott et al. 1993, Nucleic Acids Research 21:1965-1974 ("Mott") describes a heuristic filtering procedure which calculates the distance between probes (by statistical mechanics) to create a minimum-spanning subset of the probes. Mott's heuristic ordering procedure begins by identifying, for each probe, all neighboring probes (i.e., probes linked by jointly positive clones) and then orders the probes using the following algorithm. Starting with a randomly chosen probe that has not yet been fit into a set of ordered probes (which is to say it is "unordered"), either the most or, alternatively, the least distant neighbor of that probe is identified. Choosing the least distant neighbor builds a more detailed clone order, whereas choosing the most distant neighbor tends to identify a minimal set of probes connected by clones spanning large regions of DNA. If such a neighbor is found, all probes common for both neighborhoods are designated as "ordered", and the "neighbor" probe is then used as a new starting point to look for more most or least distant neighbors. Mott recognizes that false positives (such as those caused by repeated sequences) and false negatives can create problems in determining probe order. As a practical matter, when such inconsistent pieces of data are identified, they are simply ignored. Furthermore, a set of heuristic rules are applied which will identify "suspect" data.

U.S. Pat. No. 5,219,726, entitled "Physical Mapping of Complex Genomes" by Evans, filed Jun. 2, 1989 and issued Jun. 15, 1993, discloses a method of chromosome mapping which involves the simultaneous analysis of multiple cosmid clones for the detection of overlaps. Overlaps between two clones are identified by cross-hybridization rather than by comparing patterns of restriction fragments or hybridization to a panel of probes. Because this strategy does not depend on pattern recognition for detecting overlaps, analysis may be carried out on cosmid clones grouped together. No particular algorithm for ordering is provided.

3. SUMMARY OF THE INVENTION

The present invention relates to a method of ordering DNA fragments in which binary overlap information, obtained by determining whether pairs of fragments hybridize to each other, is used to build a "spanning path" across a parent DNA molecule by successively attaching cloned fragments which overlap. The relative position of the many other, non-path fragments is not essential information, but can be determined. Means for eliminating false positives and false negatives is provided. The overlap relationships between fragments may be depicted as an interval graph. The method of the present invention is time efficient and is more successful at determining the correct order of fragments than prior art methods.

3.1. Definitions

Definition 1: Let V be a finite set of intervals of a real line. Then G(V) denotes the graph whose set of vertices is V, where $v_1, v_2 \in V$ are joined by an edge, if and only if, $v_1 \cap v_2 \neq 0$. The graph G(V) is called the interval graph ("IG") associated with V.

Definition 2: Let P be a subset of V. Then G(V,P) denotes the graph whose set of vertices is V, where $v_1, v_2 \in V$ are joined by an edge if, and only if, the following two conditions are satisfied:

$$v_1 \cap v_2 \neq 0 \quad (i)$$

$$v_1 \in P \text{ or } v_2 \in P \quad (ii)$$

The elements of P are called p-vertices. The graph G(V,P) is called the probe interval graph ("PIG") associated with the pair (V,P). Note that G(V,V)=G(V), hence an interval graph may be regarded as a special kind of probe interval graph.

Definition 3: A path a along either an interval or probe interval graph is a finite sequence of vertices, $v_1, v_2 \ldots v_n$, such that $v_i$ is connected to $v_{i+1}$ by an edge for all i such that $1 \leq i \leq n-1$. The path σ is said to be a simple path if $v_i \neq v_j$ for $i \neq j$. That is, in a simple path a vertex cannot be repeated.

Definition 4: Given the sets of intervals V and V*, then V* is a cover set of V if the union of the intervals in set V is a subset of the union of the intervals in set V*. For example, vertices {36, 19, 28} is a cover set of vertex {21} (FIG. 1).

Definition 5: Let $\sigma=v_1, v_2, \ldots v_n$ be a simple path on a probe interval graph, G(V,P). Let $W=\{w_1, w_2, \ldots w_n\} \subset V$ be the set of all vertices which have a non-empty intersection with either $v_1$ or $v_n$ (the boundaries). The expanded union of σ is defined to be the union of all intervals represented by the vertices contained in W∪σ, that is, the expanded union of $\sigma = w_1 \cup w_2 \ldots \cup w_m \cup v_1 \cup v_2 \ldots \cup v_n$. Thus, in FIG. 1, σ could be the path {19, 27, 30}, and therefore the expanded union of σ includes the overlaps with the vertices {21, 23, 28, 32}. Thus the expanded union is {19, 21, 23, 27, 28, 30, 32}.

Definition 6: Given a probe interval graph G(V,P), a simple path from one p-vertex to another p-vertex is a spanning path ("SP"), that is, a path-spanning the line as described by G, if the expanded union of this path is a cover set of V, that is, if it includes the boundary vertices.

4. BRIEF DESCRIPTION OF THE DRAWINGS

FIGS. 1A–1F. Deducing a cosmid SP using hypothetical IG data. (A) Individual cosmids (numbered) labelled by T3 and T7 polymerase (filled rectangles at edges) are hybridized to the entire cosmid panel. (B) Overlap data of the hybridization results. (C) Starting with a randomly-picked cosmid (#28, boxed) as a root, the cosmid overlaps are represented as trees in two breadth-first searches. (D) Potential SP's (i.e. ordered cosmids in ovals) derived from the second breadth-first search in C (bold lines). The SP cosmids are shown as a contig (arrayed boxes); the non-SP cosmids are positioned below the SP based on the overlap data in B. The SP only indicates overlaps; no spacing between adjacent cosmids should be inferred. (E) Initial cosmid hybridization matrix, based on data in panel B. Asterisks along the main diagonal denote cosmids hybridizing to themselves; dashes denote all other cosmid—cosmid hybridization pairs. (F) Reordered matrix. SP-member cosmids are in bold. Notation as in E.

FIGS. 2A–2F. Deducing a cosmid SP using hypothetical PIG data. (A) Cosmids 17, 19, 31, and 32 are not probes. (B) These non-probe cosmids are not listed in the initial overlap data set (left), but most of their overlap relationships can be deduced by inspection of the initial overlap data (right). Only the overlap between non-probe cosmids 17 and 31 cannot be inferred. (C) Breadth-first search trees. (D) An SP. Note that although cosmid 31 is the deepest vertex, it is not the deepest p-vertex, and is therefore not included in the SP. (E) The initial hybridization matrix. The four non-probe cosmids are included as gaps in the matrix for clarity. (F) Reordered matrix. Note the close similarity to the reordered matrix in FIG 1F. Other notation as in FIG. 1.

FIGS. 3A–3H. False joins in an IG due to repetitive elements. (A) A probe cosmid (#30) containing a labelled repetitive element (shaded circle) hybridizes to other cosmids (bold labels) harboring the same (unlabelled) repetitive element (open circles). Note non-reciprocal hybridizations between cosmid pairs 30-17, 30-31, and 30-33. (B) Two non-overlapping probe cosmids (#31 and #32) containing a labelled repetitive element (shaded circles) hybridize to other cosmids harboring the same (unlabelled) repetitive element (open circles). Note the cosmids 31 and 32 constitute a false reciprocal hybridization pair. (C) Overlap data from the arrangement in B. The non-reciprocal cosmid pairs (indicated by strikethroughs) are not used in building the trees. (D) Breadth-first search trees using the data in C. (E) Generation of a path which is not an SP. (F) Removal of the vertex with the most edges (cosmid 31) from the table of overlap data (strikethrough lines). (G) Recalculation of the two breadth-first searches in the absence of cosmid 31. (H) The resulting SP. Note that this SP agrees perfectly with that in FIG. 1, even though the breadth-first search trees are slightly different. Other notation as in FIG. 1.

Figure 4A:
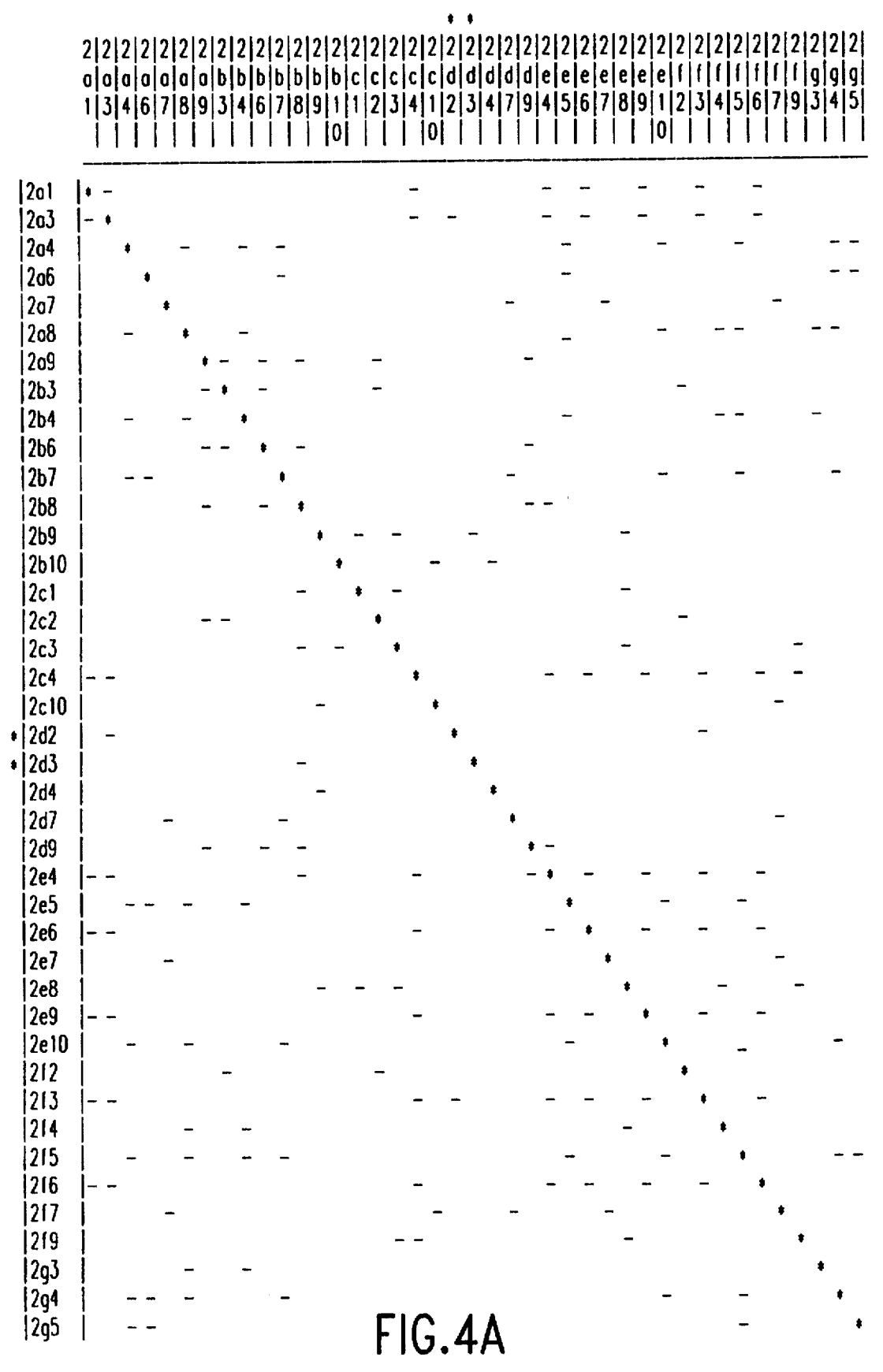
Figure 4C:
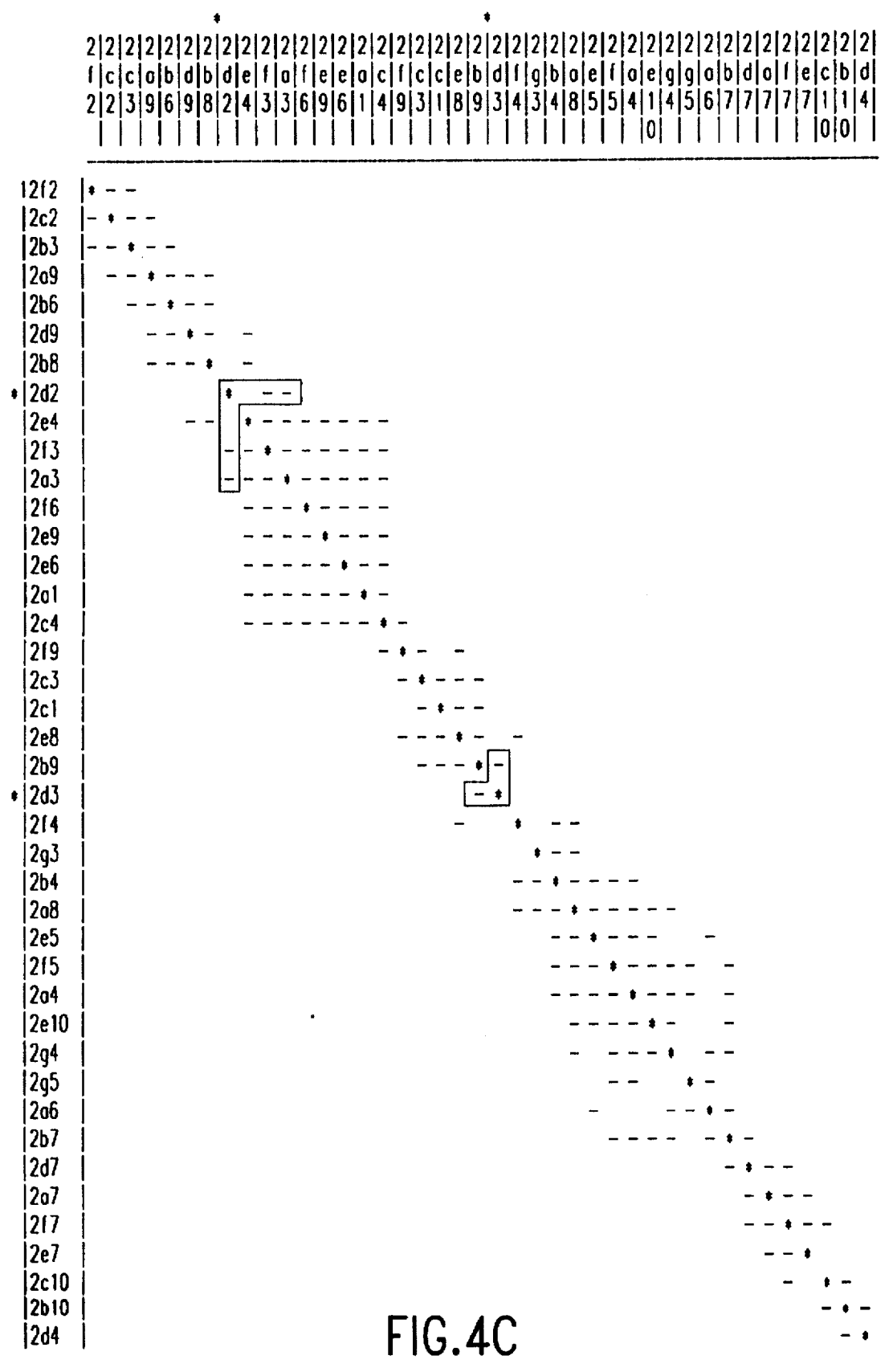

FIGS. 4A–4C. Application of the algorithm to deduce a cosmid SP for YAC2 on human chromosome 13. (A) Initial cosmid matrix hybridization data. Cosmid numbers are listed at the top and left sides. Notation of cross-hybridizing cosmids as in FIG. 1. Dots denote two non-SP cosmids that required more than one iteration of the weighting scheme in order to position them on YAC2. (B) One spanning path using the cosmids identified in B. The order of the cosmids is based on the breadth-first searches. The SP only indicates overlaps; no spacing between adjacent cosmids should be inferred. (C) Rearranged hybridization matrix after application of the SP algorithm. Note that the rearrangement places the hybridization data along the main diagonal, as expected. The positions of the two reweighted cosmids noted in A are shown (dots and boxes). Other notation as in FIG. 1.

5. DETAILED DESCRIPTION OF THE INVENTION

The present invention provides a method of ordering DNA fragments which does not rely on the analysis of complicated restriction fragment fingerprints or digital signatures reflecting hybridization profiles, but which produces so-called binary overlap information by answering Yes or No to the following question: for each pair of fragments considered, do these fragments hybridize to each other? Moreover, the present invention does not require that all cloned fragments available be ordered, but rather builds a "spanning path" across the parent DNA molecule by successively attaching cloned fragments which overlap. The relative position of the many other, non-path fragments is not essential information, but can be determined.

According to the present invention, each element analyzed may be represented in graphical form. A DNA molecule may be represented as an interval spanned by cloned fragments. "Vertices" correspond to the intervals spanned by clones (i.e., the cloned fragments of the parent DNA molecule) and "edges" correspond to overlaps between pairs of clones.

The overlap relationships between fragments may be graphically depicted. A series of overlapping clones is called a "contig". If every clone were used as a probe, and each clone were detectably labeled across its entire length so that all possible overlapping clones would be identified by hybridization, an "interval graph" ("IG") would be generated. If only a portion of the clone collection is used to prepare probes, then the hybridizing pairs of clones represent only a subset of all theoretically possible overlaps, but can be used to generate a contig map called a probe interval graph ("PIG").

According to the present invention, a collection of clones is obtained which are prepared from a parent DNA molecule of interest. Preferably, the number of clones in the collection (hitherto referred to as a "library") is such that the entire parent molecule is represented at least once, and preferably several times (i.e., the library is redundant). Individual clones are then hybridized to detectably labeled probes which are themselves prepared from individual clones in the collection. This process determines whether each member of a pair of clones hybridizes to the other. In a non-limiting specific embodiment of the present invention, the probes correspond to the ends of a cloned fragment and are produced using T3 and/or T7 priming sites at the end regions of the fragment, that is to say, at the vector/fragment boundaries. The term "end region" as used herein refers to about 50–100 nucleotides at the beginning or end of a fragment. If two cloned fragments hybridize to each other, an overlap is postulated. For example, and not by way of limitation, FIG. 1B depicts the results of hybridization tests between a series of hypothetical cloned fragments (in which the cloning vector is a cosmid).

Once the hybridization results are obtained, they may be used to construct a spanning path by building a "tree" of fragments produced by joining fragments that hybridize to one another. Any one of the clones analyzed can be used to start the tree; this clone is referred to as the "root vertex". Clones which hybridize to the root vertex are identified and form the next level of the tree; clones which hybridize to them, except for the root vertex, form the next level, and so forth, until a "dead end" is reached, but each clone is represented only once in the tree. This process of tree-building is referred to as a breadth-first search (Golumbic, 1980, "Algorithmic Graph Theory and the Perfect Graph", Academic Press, New York; and see, for example, FIG. 1C). The root vertex temporarily defines one end of the contig, but the highest level of the tree contains a true boundary cloned fragment. By performing a second breadth-first search using this true boundary fragment, the boundary fragment at the other end of the contig may be identified. If more than one fragment lies at the highest level of a tree produced by either breadth-first search, more than one spanning path may be deduced.

The foregoing analysis may be further modified, according to the present invention, to account for the real-life problems of falsely positive and falsely negative hybridizations. First, because even clones which do not truly hybridize to a probe produce a background level of detectable signal, a clone which does not actually hybridize to a probe may nevertheless be scored as a (false) positive for hybridization. Similarly, a clone/probe pair which actually do hybridize may be read as a (false) negative. Moreover, most DNA sequences are peppered with "repeated DNA sequences" at regular intervals. Families of repeated sequences exist that are represented many thousands of times in a single chromosome. Therefore, a probe may hybridize to a clone because it contains a repeated sequence which is also present in the cloned fragment, not because of true clone overlap.

The present invention deals with these problems by ignoring pairs of clones which do not exhibit reciprocal hybridization. Such non-reciprocal pairs may be eliminated from the data set prior to breadth-first analysis. But if repeated sequences are shared among two or more probes, false reciprocal results may be obtained. The present invention tests for false overlaps by determining whether at least one spanning path can be constructed from an interval graph or probe interval graph. If no one spanning path can be constructed, it may be assumed that there is an inconsistency in the data set. In this case, one or more clones (vertices) may be eliminated from the data set, with clones which are more likely to contain repeated elements being deleted first. Such clones typically hybridize to a particularly large number of other clones (that is to say, they have the most edges). "Suspicious" clones may be eliminated until a spanning path is constructed.

Importantly, when the collection of clones being analyzed—the clone library—is highly redundant, the ability to detect a spanning path is not affected by eliminating a few clones from the data set. The combination of a stringent algorithmic requirement and a highly redundant library enable the generation of relatively unambiguous contigs.

It should also be noted that the method of the present invention provides for the formation of a spanning path from an incomplete data set, one in which hybridization of all clone/clone pairs has not been tested. A hypothetical analysis using partial overlap data is depicted in FIG. 2. This enables the construction of a useful map with less data, saving valuable laboratory time.

Once one or more spanning paths are obtained, each can be used to reorder the original clone-hybridization matrix. This is performed using a weighted distance scheme, in which the first clone in the spanning path is assigned a weight of 1, the second is assigned a weight of 2, and so forth. For clones which are not included in the spanning path, each is inspected individually, and is assigned a weight which is the average of the weights of spanning path clones which it overlaps. A reordered matrix generated using this scheme may then be graphically represented (see, for example, FIG. 1F).

This matrix offers a number of advantages. First, it allows one to visualize the location of all the cloned fragments in a contig. Second, it permits the identification of "weak points" in the contig where only a relatively few cloned fragments reside. Third, it provides a representation of the "clonability" of specific regions of the parent DNA. Fourth, such a matrix allows the identification of cloned fragments for sequencing as a source of statistically-spaced sequence tagged sites ("STSs").

In a preferred, specific, non-limiting embodiment, the method of the present invention may be practiced using the source code contained in the Microfiche Appendix, which is in the C language and may be used with a Convex C-220 computer running the Convex Unix operating system.

For example, and not by way of limitation, the method of the present invention has been applied to matrix hybridization data generated for assembling cosmid and YAC contigs representing regions of human chromosome 13, as described in greater detail below. In particular, the algorithm was used to deduce a cosmid contig spanning YAC2, a YAC localized to human chromosome 13. A collection of 67 cosmid clones were initially identified as containing YAC2 sequence. During generation of the cosmid hybridization matrix, 24 of the 67 cosmids failed to hybridize with any other cosmid, and were eliminated from further analysis by the algorithm. The remaining 43 cosmids were used to generate two contigs, one consisting of a string of 41 cosmids, and the other, of two cosmids.

Certain features of this working example are noteworthy. First, the YAC contig was generated using only partial overlap data. Second, only 17 of the 41 cosmids were required to generate the spanning path. Third, two non-path cosmids that were not ordered based on the initial weighted distance scheme were ordered after a reiteration of the weighting scheme.

EXAMPLE: AN ALGORITHM BASED ON GRAPH THEORY FOR THE ASSEMBLY OF CONTIGS IN PHYSICAL MAPPING OF DNA

6.1. The Algorithm

In the strategy to isolate YAC and cosmid contigs on chromosome 13 a YAC that has been identified to represent a segment of chromosome 13 is used as a hybridization probe of a chromosome 13-specific cosmid library to isolate the 40–50 cosmids representing regions on the YAC. DNA from each of the cosmids is spotted in an array on a filter. The insert of each cosmid is labeled at its edges using T3 and T7 polymerase priming sites at the vector/insert boundaries, and the filter is hybridized with each of the approximately 50 probes to identify groups of cosmids which overlap each other in the cosmid hybridization matrix. The present invention may be used to reorder the matrix in such a way that all overlapping cosmids are ordered along the length of the YAC.

The cosmid matrix hybridization method produces binary overlap information, by answering Yes or No to the following question: For each pair of fragments considered, do these two fragments overlap? Earlier approaches to ordering sequence fragments from binary overlap data attempted to compute the comprehensive arrangement of all fragments using interval graphs (Booth and Luecker, 1976, J. Comput. System Sci. 13:335–379; Rose et al., 1976, SIAM J. Comput. 5:266–283; Korte and Mohring, 1989, SIAM J. Comput, 18:68–81). A PQ-tree algorithm based on an IG will compute this order in linear time with respect to the number of overlapping fragments (Booth and Luecker, 1976, supra). However, it was unclear whether the same linearity also applied in the case where not all the data are used in the analysis. This question is relevant to cosmid contig mapping, because the mapping task could be made more efficient if one could reorder the overlapping cosmids using only a subset of the cosmids in the cosmid-hybridization matrix.

A subset of cosmid probes is graphically represented as a probe interval graph (PIG). This working example demonstrates that: (1) an ordering of cosmids along the YAC can be accomplished, and (2) such an ordering can be computed in a time that is linear with respect to fragment number.

Thus, according to the invention establishing the complete arrangement of all mutually overlapping fragments is not necessary. Importantly, to determine the approximate placement of markers along the chromosome, where those markers have already been localized to specific fragments, it is only necessary to construct a "path" through the pattern of fragments, building it by successively attaching fragments which overlap each other. A connected series of fragments spanning the sequence region of interest is called a "Spanning Path," or SP. For marker placement purposes, the relative position of the many other, non-path fragments is of minor consequence, as knowing the location of the non-path fragments would provide little additional mapping information. One can, however, relate all non-path cosmids to the SP cosmids, thereby obtaining information about the relative linear arrangement and location of all the cosmids.

The method for identifying an SP, given pairwise overlap data as input, is embodied in an interval graph, which represents effectively the overlap relationships between all fragments. It is easiest to present the method by illustrating the evolution of an overlap graph as a particular set of hypothetical data is analyzed. Section 3.1., supra, contains the definitions upon which this analysis is based.

Consider the configuration of cosmid clones depicted schematically in FIG. 1A. Each cosmid's insert is represented by a numbered horizontal segment. The labelled segments at the ends of the cosmids, which are used as probes in the hybridization, are represented by the thick lines. Of course, this arrangement of overlapping cosmids is not known initially. From the matrix hybridization data, a list of cosmid-cosmid overlaps can be generated (FIG. 1B).

Note that this example is an IG, as all the cosmids have been used as probes. Note also that in the example presented here, all possible cosmid hybridization pairs have a reciprocal relationship to each other (e.g. cosmid 27 hybridizes to cosmid 32, and reciprocally, 32 hybridizes to 27). This reciprocity is always true in an IG in which the cosmids are labelled across their entire length. However, in the more restrictive case where the cosmids are labeled only at their edges, reciprocity is usually, but not always, true. This issue, which has implications for the analysis of both false positive and false negatives, is discussed in greater detail below.

Next, one cosmid is picked at random (cosmid #28 in this example). A tree is built using this cosmid as the root vertex, as follows. The algorithm examines the overlap list (FIG. 1B) to identify the other fragments that overlap cosmid 28 (cosmids 19, 21, and 36 in this example). These cosmids become new second-order vertices in the tree, occupying a new row beneath the root vertex, with the lines between the vertices indicating the presence of an overlap. The process continues, using each cosmid only once, until a complete tree is built. Thus, cosmid 19 is known to overlap cosmids 21, 27, and 28, but 21 and 28 were encountered earlier in the construction, so only 27 is attached at the next level. Cosmid 21 is not found to have any more overlaps, so its branch is declared a dead end. Cosmid 36 has an additional overlap with 17. This process continues until all branches of the downward-growing tree are exhausted. Only downward overlap links are added in building the tree; any overlaps between cosmids with same- or higher-level nodes are ignored. Note that one of the cosmids identified at the deepest level of the tree (cosmid 24) is located at one boundary of the contig, while the randomly-chosen root vertex (cosmid 28) is, temporarily, the other boundary of the contig, that is, the spanning paths are only partially defined. The process of building the tree is referred to as a breadth-first search (Golumbic, M. C. 1980, in "Algorithm Graph Theory And The Perfect Graph", Academic Press, New York).

At this point, a second breadth-first tree is constructed, beginning with the lowest and second-lowest branches in the initial tree (since one cannot determine which of these branches is a boundary, both must be selected). In this particular example there is only a single lowest branch, cosmid 24 (boxed in FIG. 1C). Having rebuilt the tree in the second breadth-first search from a boundary vertex, the algorithm concludes by choosing any vertex at the lowest level of the rebuilt tree (cosmids 31 or 33 in this example), which is potentially located at the other boundary of the contig (Definition 5, Section 3.1).

In other words, starting with a randomly-chosen cosmid, the first breadth-first search identifies the cosmid(s) at one end of the contig, and those ends become the starting root(s) for the second breadth-first searches to identify the cosmid (s) located at the opposite end of the contig. As the second breadth-first search tree contains all the cosmids encountered between the two boundaries in hierarchical order, all spanning paths can be traced up the tree between the boundaries. In this example, there are two possible SPs (Definition 6, Section 3.1; FIG. 1D). In this particular case, given only binary data, it is not possible to determine which cosmid (31 or 33 at the left end; 23 or 24 at the right end) is at the true boundary.

As noted above, labelling cosmids only at their edges can result in non-reciprocal cosmid hybridization pairs. For example, if cosmid x is located entirely inside of cosmid y, x will certainly hybridize to y, but y may not hybridize to x, because cosmid y is labelled only at its end and its probe cannot identify cosmid x. Since, in the case of an IG, all the cosmids are used as probes, the reciprocal relationship between cosmids x and y can still be inferred (i.e. if x identifies y, then y should identify x). However, non-reciprocal hybridization "hits" between cosmid probe pairs may be ignored according to the invention, for the simple reason that it is unknown whether such non-reciprocity is real (e.g. cosmid x lies completely inside cosmid y) or artifactual (e.g. cosmid x is a false positive, or conversely, cosmid y is a false negative). As indicated below, non-reciprocal hybridization is not ignored when a member of the cosmid pair is not a probe.

Given the redundancy in the YAC and cosmid libraries, this requirement for reciprocity between cosmid probes is, in fact, a powerful tool to eliminate false overlaps caused by repetitive elements. For example, FIG. 3A shows a hypothetical situation in which one probe on cosmid 30 contains a repetitive element (shaded) that hybridizes to 5 other cosmids (17, 27, 31, 32, 33), three of which (cosmids 17, 31, and 33) are not authentic overlaps. Because there is no reciprocity between cosmid 30-17, 30-31, or 30-33, those three pairs are eliminated from the data set (note that authentic overlaps between 30-27 and 30-32 exist, whether or not the repetitive element is present). Once these three non-reciprocal cosmid probe pairs have been eliminated, it is easy to show that a correct SP can be generated.

FIG. 2 illustrates the extension of this approach to a situation in which only partial overlap data are available. In accordance with Definition 2 (Section 3.1, supra), such a situation generates a probe interval graph (PIG), because even though most overlaps can be deduced by reciprocity, overlap 17-31 remains undetected (FIG. 2B). Nevertheless, by following the same approach as described for the IG, a spanning path can be deduced.

One can still have a situation in which a repetitive element is shared among two or more probes, thus generating false reciprocal hybridization data (e.g. cosmids 31 and 32 in FIG. 3B). However, this problem can be dealt with. The present invention employs a simple test for false overlaps. If at least one SP cannot be constructed from the IG or PIG, an inconsistency in the data set is claimed. It is easy to prove that for a PIG (and certainly for an IG), there is at least one SP in the set of paths generated by the algorithm. With false positive caused by repetitive elements, the set of paths generated (only one such path in this example, 36-28-19-27-30-23-24; FIG. 3E) may not contain at least one SP (see Definition 6 in Section 3.1., supra). Thus, the failure to find an SP enables the recognition of false positives.

When an SP is not found, a heuristic method may be used to find an SP, by eliminating some vertices from the data set. The most likely vertex to eliminate is that which has the largest number of edges, because it is the presence of the repetitive element that gives rise to these "extra" edges. In this example, cosmid 31 is eliminated (FIG. 3F). By doing so, the reconstructed tree (FIG. 3G) generates an SP (FIG. 3H), which, in fact, agrees with the SP shown in FIG. 1. If this procedure fails, another vertex with the next greatest number of edges may be eliminated and a repeat analysis may then be performed.

In dealing with multi-fold clone libraries (e.g. a cosmid library with 5x coverage), the ability to detect an SP is not affected by eliminating a few cosmids from the data set. Thus, the combination of a stringent algorithmic requirement plus a highly redundant cosmid library enables the generation of relatively unambiguous contigs.

Once one or more SPs are obtained, each can be used as a framework for reordering the original cosmid-hybridization matrix (FIG. 1E) according to distance along the YAC. This reordering of the matrix is done by a "weighted distance" scheme, as follows (see the example of FIG. 1).

1. Every cosmid in the SP is given a "weighted distance" corresponding to its order in the path. For example, in the first SP shown in FIG. 1D (i.e. 31-17-36-28-19-27-30-23-24), cosmid 31 has weight 1, cosmid 17 has weight 2, and so on, with cosmid 24 having weight 9.

2. For the remaining non-path cosmids (i.e. 21, 32 and 33), each cosmid is inspected individually. If it overlaps with one or more SP-member cosmids (see FIG. 1B), its weight is counted as the average of the weighted distances of the SP-member cosmids that it overlaps. For example, non-path cosmid 21 has a weighted distance of 4.5, as it overlaps cosmids 19 (weight 5) and 28 (weight 4). Similarly, cosmid 32 has a weighted distance of 6.5 (average of distances 6 [cosmid 27] and 7 [cosmid 30]; and cosmid 33 has a distance of 1.5 (average of distances 1 [cosmid 31] and 2[cosmid 17]).

3. The weighted distances of the non-SP cosmids generated in step 2 are added at the appropriate positions to the list generated in step 1. Thus, the weighted distances are now: 1 (cosmid 31), 1.5(33), 2(17), 3(36), 4(28), 4.5(21), 5(19), 6(27), 6.5(32), 7(30), 8(23), and 9(24). Sometimes two cosmids may have the same value; in that case they are arranged in alphanumeric order.

4. In our example, all 12 cosmids have now been ordered, as each of the three non-SP cosmids overlaps at least one SP-member cosmid. However, there may be cases where there are no data available to indicate where a non-SP cosmid overlaps any SP-member cosmid (e.g. as a result of false negatives, or in the case where only a subset of cosmids are available as probes). In these situations, each of these initially-unordered cosmids is assigned a weighted distance equal to that of the first non-SP cosmid in the order with which it overlaps, and is placed in the order immediately following that cosmid.

5. In step 3, we weighted those non-SP cosmids that had a direct relationship only to SP-cosmids. However, there may be situations where a non-SP cosmid hybridizes to both an SP- and non-SP cosmid. The weighting of such a cosmid proceeds in two stages. First, it is assigned an initial (average) weight based on its relationship to the SP-only cosmid, prior to the reweighting of non-SP cosmids in step 3. Second, it is reweighted based on its relationship to all the cosmids (i.e. SP and non-SP) following the reweighting in step 3. The new list is now renumbered in order.

6. For large data sets, step 5 may need to be reiterated once or twice before a stable order is reached.

Figures 1E, 1F:
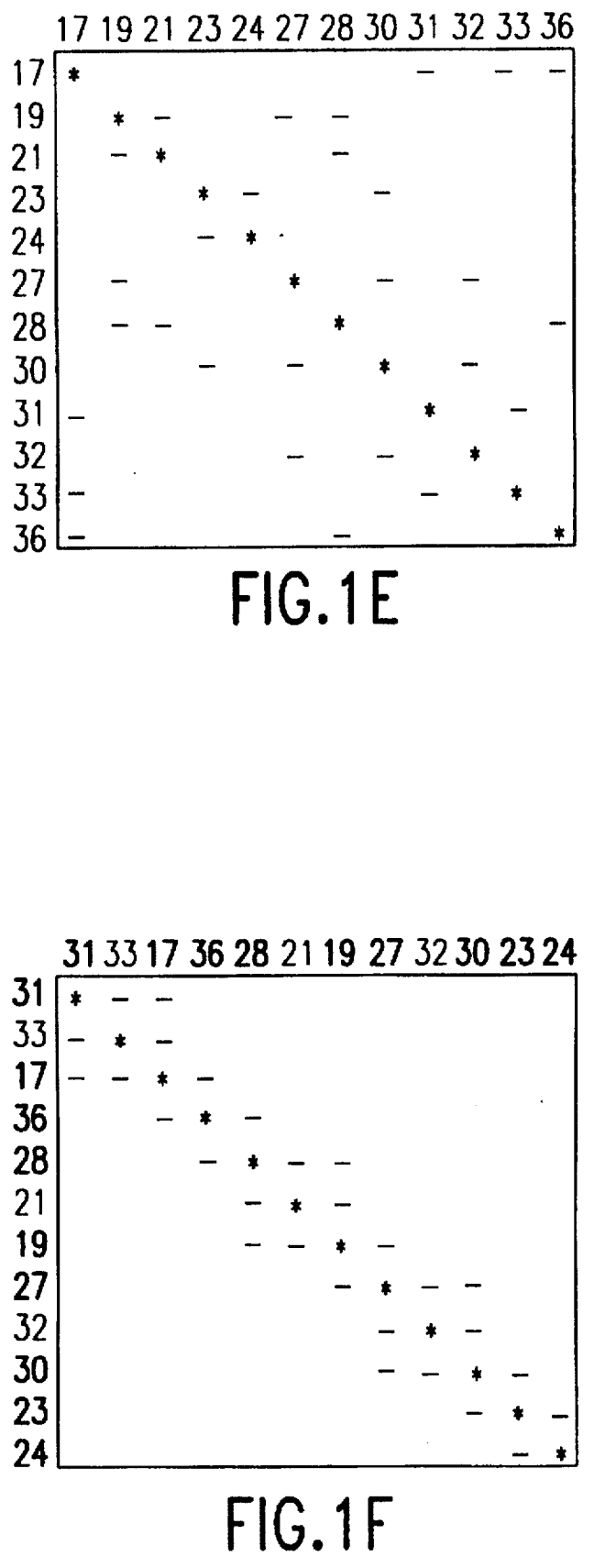

The reordered matrix based on this scheme (FIG. 1F) shows all the cosmids (that is, both those contributing to the SP [shown in bold in FIG. 1F] and those not contributing to the SP) arranged contiguously along the length of the YAC. The advantage of this matrix is that it allows one to: (1) visualize the location of all the cosmids in the contig, (2) identify "weak points" in the contig where only a relatively few number of cosmids reside, (3) visualize the representation of the cosmid library and the "clonability" of certain regions, and (4) identify cosmids for sequencing as a source of statistically-spaced STS's.

The CPU time required for one breadth-first search is approximately linear with respect to the sum of the number of vertices (i.e. cosmids) and edges (i.e. cosmid overlaps) in the graph. However, this does not mean that the overall algorithm is linear with respect to the number of cosmids analyzed, because with multiple potential boundaries more than just two breadth-first searches are required to establish all possible SPs. The maximum number of such searches is of course less than the number of cosmids analyzed. Thus, the lower bound of the algorithmic complexity is linear; the upper bound is quadratic.

The algorithm was coded in the C language on a Convex C-220 running the Convex Unix operating system. The code is portable to most computers with a C compiler. The copyrighted program is available as a Microfiche Appendix.

6.2 Application to Physical Mapping of Human Chromosome 13

The algorithm has been applied to matrix hybridization data generated for assembling cosmid and YAC contigs representing regions of chromosome 13. We have implemented this algorithm for two different but related sets of data; (1) overlapping cosmids spanning a YAC in order to generate a cosmid contig, and (2) fingerprints of cosmid data spanning two different but overlapping YACs in order to generate a YAC contig.

We show here an example of the application of the algorithm for deducing a cosmid contig spanning YAC2, a YAC localized to human chromosome 13.

The binary overlap data from the cosmid—cosmid overlap table of YAC2 and its associated hybridization matrix were the input to the algorithm. Alu-PCR hybridization of YAC2 to the cosmid library identified 67 cosmids. During generation of the cosmid hybridization matrix, 24 of the 67 cosmids identified no other cosmids, and were eliminated from further analysis by the algorithm. The remaining 43 cosmids were analyzed by the algorithm, and generated two contigs, one of 41 cosmids and one of two cosmids (i.e. two "islands" along YAC2). Only the 41-cosmid contig is displayed here, first as a hybridization matrix (FIG. 4A), then as a spanning path (FIG. 4B), and finally as a reordered matrix (FIG. 4C).

Certain features of this example are noteworthy. First a YAC contig was generated using only partial overlap data (using a PIG). Second, only 17 of the 41 cosmids were required to generate the SP (FIG. 4B). Third, when the SP was generated, two non-path cosmids, $2d2$ and $2d3$, were identified that were not ordered based on the initial weighted-distance scheme using steps 1–3 above (see FIG. 4C): cosmid $2d2$ hybridized only to non-SP cosmids $2f3$ and $2a3$; cosmid $2d3$ hybridized only to non-path cosmid $2b9$. These two cosmids were ordered after a reiteration of the weighting scheme (steps 4–6 above).

Alignment of the 41 cosmids spanning YAC2 derived from the initial 67 cosmids took 0.28 seconds of CPU time on a Convex 220 computer. An alignment of 202 cosmids spanning a 3-YAC contig took 1.35 seconds of CPU time, and 433 cosmids took 3.15 sec.

6.3 Discussion

The described algorithm simplifies the logical process of deducing spanning paths, by transforming the overlap data into a graph abstraction. Importantly, the time required to conduct each breadth-first search is approximately linear with respect to the number of vertices and edges. Thus, for most practical problems, the SPs can be deduced in a few seconds of CPU time. All of the cosmids (both SP- and non-SP members) can be ordered along the length of the contig by weighting each cosmid in relation to its proximity to a terminal cosmid.

The SPs derived from hypothetical and experimental data can be obtained via probe data not revealing all of the true cosmid—cosmid overlaps, that is, by using a PIG rather than an IG. This is especially true for overlap data obtained from robust cosmid and YAC libraries, which are deliberately created with 3x–5x fragement densities to minimize gaps in their sequence coverage.

Ideally, the algorithm should have the ability to deal with false negatives and false positives. False negatives (absence of a hybridization signal between two cosmids which do overlap) usually present no problem to the construction of an SP, due to the redundancy of clones in 3x- to 5x-deep YA and cosmid libraries. On the other hand, false positives (presence of a hybridization signal between two cosmids which do not overlap), which can arise due to cross-hybridization between repetitive elements, can present a serious problem which must be dealt with. A false positive may produce an erroneous edge in the IG or PIG. Thus, any breadth-first search which uses those edges may result in an incorrect SP. The present invention addresses this problem by requiring that all pairs of cosmid overlaps be reciprocal, that is, if cosmid x hybridizes to cosmid y, then y must hybridize to x. If reciprocity is not achieved, that particular overlap is eliminated from the data set. From a practical standpoint, however, hybridization with excess cold competitor DNA reduces significantly the number of false overlaps due to repetitive elements. Thus, good experimental technique, coupled with highly-redundant libraries, enables the generation of complete contig maps with little loss in efficiency.

The data on the chromosome 13 cosmid contigs analyzed to date confirm the linearity of the algorithm, at least when the number of cosmids being analyzed is relatively small. However, there will probably be circumstances in which there are deviations from linearity. For a segment of DNA as large as chromosome 13 (approximately 100 mb), the program may theoretically be able to calculate a complete 10,000-cosmid contig across the entire chromosome in approximately 2 minutes, assuming linearity, however, even if a quadratic relationship between CPUs and cosmid number existed, the CPU time would be only 1–2 hours.

Various publications are cited herein, which are hereby incorporated by reference in their entirety.

What is claimed is:

1. A method of preparing a map of a parent DNA molecule, said method comprising the following steps:

(i) cleaving more than one copy of the parent DNA molecule such that different copies are cleaved at different points to generate a plurality of fragments wherein at least some of the fragments overlap;

(ii) subcloning the fragments and arranging the subclones in pairs;

(iii) performing hybridization reactions with each pair of subclones to be considered, thereby generating binary overlap data which identifies the pairs of subclones that hybridize to each other, and forming the binary overlap data into a clone-hybridization matrix;

(iv) building a first conceptual tree of the subclones from the clone-hybridization matrix obtained in step (iii), starting with any subclone as the root vertex of the first tree, by (a) identifying a first set of the subclones which overlap the root vertex of the first tree, thereby forming a first level of the first tree;

(b) forming the next level of the first tree by identifying a next set of the subclones which overlap at least one subclone of the previous level, but where no subclone is listed in more than one level; and (c) repeating step (iv)(b) until no further subclones can be identified which overlap at least one subclone of the previous level and have not already been listed, so that the first tree is completed and the previous level of the first tree contains a set of one or more first boundary subclones;

(v) building a second conceptual tree of the subclones from the clone-hybridization matrix obtained in step (iii) using, as the root vertex of the second tree, a first boundary subclone identified in step (iv), by (a) identifying a first set of the subclones which overlap the root vertex of the second tree, thereby forming a first level of the second tree;

(b) forming the next level of the second tree by identifying a next set of the subclones which overlap at least one subclone of the previous level, but where no subclone is listed in more than one level; and (c) repeating step (v)(b) until no further subclones can be identified which overlap at least one subclone of the previous level and have not already been listed, so that the second tree is completed and the previous level of the second tree contains a set of one or more second boundary subclones;

(vi) attempting to form a spanning path, where said spanning path extends from a second boundary subclone identified in step (v), through a series of consecutive subclones from successive levels of the second tree, wherein each consecutive subclone overlaps both the subclone which precedes it as well as the subclone that follows it in the series, to the first boundary subclone, and wherein the spanning path cannot thus be formed;

(vii) identifying the subclone in the second tree which cross-hybridizes to the greatest number of the other subclones in the second tree;

(viii) eliminating the subclone identified in step (vii) from the second tree;

(ix) attempting to form the spanning path, if the spanning path cannot be formed, then steps (vii) to (ix) are repeated until the spanning path can be formed; and (x) forming the spanning path into a map of the parent DNA molecule.

2. The method according to claim 1, wherein each hybridization reaction is performed by hybridizing both subclones in the pair with a probe which is produced by transcription from a T3 promoter at the end region of one of the subclones in the pair.

3. The method according to claim 1, wherein each hybridization reaction is performed by hybridizing both subclones in the pair with a probe which is produced by transcription from a T7 promoter at the end region of one of the subclones in the pair.

4. The method according to claim 1, further comprising eliminating from the clone-hybridization matrix, prior to step (iv), pairs of subclones which do not exhibit reciprocal hybridization.

5. The method according to claim 2, further comprising eliminating from the clone-hybridization matrix, prior to step (iv), pairs of subclones which do not exhibit reciprocal hybridization.

6. The method according to claim 3, further comprising eliminating from the clone-hybridization matrix, prior to step (iv), pairs of subclones which do not exhibit reciprocal hybridization.

7. The method according to claim 1, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

8. The method according to claim 2, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

9. The method according to claim 3, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

10. The method according to claim 4, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

11. The method according to claim 5, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

12. The method according to claim 6, further comprising making a graph of the locations of the subclones in the map by the steps comprising reordering the clone-hybridization matrix by means of a weighted distance scheme, said weighted distance scheme comprising assigning each subclone in the spanning path a weight which is equal to the order of the subclone in the spanning path, and forming the reordered clone-hybridization matrix into a graph.

* * * * *

UNITED STATES PATENT AND TRADEMARK OFFICE
CERTIFICATE OF CORRECTION

PATENT NO. : 5,667,970

DATED : September 16, 1997

INVENTOR(S) : Peisen Zhang

It is certified that error appears in the above-identified patent and that said Letters Patent is hereby corrected as shown below:

On title page
Item [56]   8th line "Meeing" should read --Meeting--;

Col. 3, line 25, "path a" should read --path σ--.

Signed and Sealed this

Fourteenth Day of July, 1998

Attest:

BRUCE LEHMAN

Attesting Officer     Commissioner of Patents and Trademarks